United States Patent [19]
Rhee et al.

[11] Patent Number: 6,019,739
[45] Date of Patent: Feb. 1, 2000

[54] MINIMALLY INVASIVE VALVE ANNULUS SIZER

[75] Inventors: Richard S. Rhee, Diamond Bar; Keith E. Myers, Lake Forest; Jerry L. Jackman, Tustin, all of Calif.

[73] Assignee: Baxter International Inc., Deerfield, Ill.

[21] Appl. No.: 09/099,732

[22] Filed: Jun. 18, 1998

[51] Int. Cl.⁷ .................................................. A61B 5/103
[52] U.S. Cl. .............................. 600/587; 623/2; 606/148; 33/512
[58] Field of Search ................................ 600/587; 623/2; 606/148, 150; 33/511, 512

[56] References Cited

U.S. PATENT DOCUMENTS

| | | | |
|---|---|---|---|
| 4,211,241 | 7/1980 | Kaster et al. | 128/774 |
| 4,441,216 | 4/1984 | Ionescu et al. | 3/1.5 |
| 4,626,255 | 12/1986 | Reichart et al. | 623/2 |
| 5,042,161 | 8/1991 | Hodge | 33/501.45 |
| 5,290,300 | 3/1994 | Cosgrove et al. | 606/148 |
| 5,360,014 | 11/1994 | Sauter et al. | 128/774 |
| 5,489,296 | 2/1996 | Love et al. | 623/2 |
| 5,531,785 | 7/1996 | Love et al. | 623/2 |
| 5,653,749 | 8/1997 | Love et al. | 623/2 |
| 5,814,096 | 9/1998 | Lam et al. | 600/587 |
| 5,814,097 | 9/1998 | Sterman et al. | 623/2 |
| 5,814,098 | 9/1998 | Hinnenkamp et al. | 623/2 |
| 5,843,177 | 12/1998 | Vanney et al. | 623/2 |
| 5,885,228 | 3/1999 | Rosenman et al. | 600/587 |

FOREIGN PATENT DOCUMENTS 2083362  3/1982  United Kingdom .

OTHER PUBLICATIONS

Booklet entitled "Carpentier–Edwards® Pericardial Bioprostheses Mini–Symposium", Chicago, IL, Baxter Healthcare Corporation, Edwards CVS Division, Apr. 24, 1993; pp 51–62, "Sizing and Implantation".

Brochure entitled "Judge Our Pericardila Valve by its Appearance and You Will Only Get Half the Picture", Edwards CVS Division, Baxter Healthcare Corporation, 1969.

*Primary Examiner*—Max Hindenburg
*Assistant Examiner*—Charles Marmor, II
*Attorney, Agent, or Firm*—Erik K. Satermo; James W. Inskeep; Guy L. Cumberbatch

[57] ABSTRACT

An annulus sizer measures the size of a valve annulus during annuloplasty surgery. The annulus sizer includes a sizing portion for measuring the valve annulus and a coupling portion for attaching to a handle. The coupling portion is disposed on a proximal surface of the sizing portion. The sizing portion has a thickness on the order of about 0.1 inch. This relatively small thickness of the sizer facilitates minimally invasive annuloplasty surgery. For example, the sizer may be inserted through a relatively small intercostal incision. In addition, the relatively thin sizing portion minimizes optical distortion. The coupling portion may be disposed on the sizing portion at a location which is offset from the center of the sizer, thereby defining an enlarged viewing area. The coupling portion may have threading to engage with threading of the handle to ensure secure attachment.

39 Claims, 2 Drawing Sheets

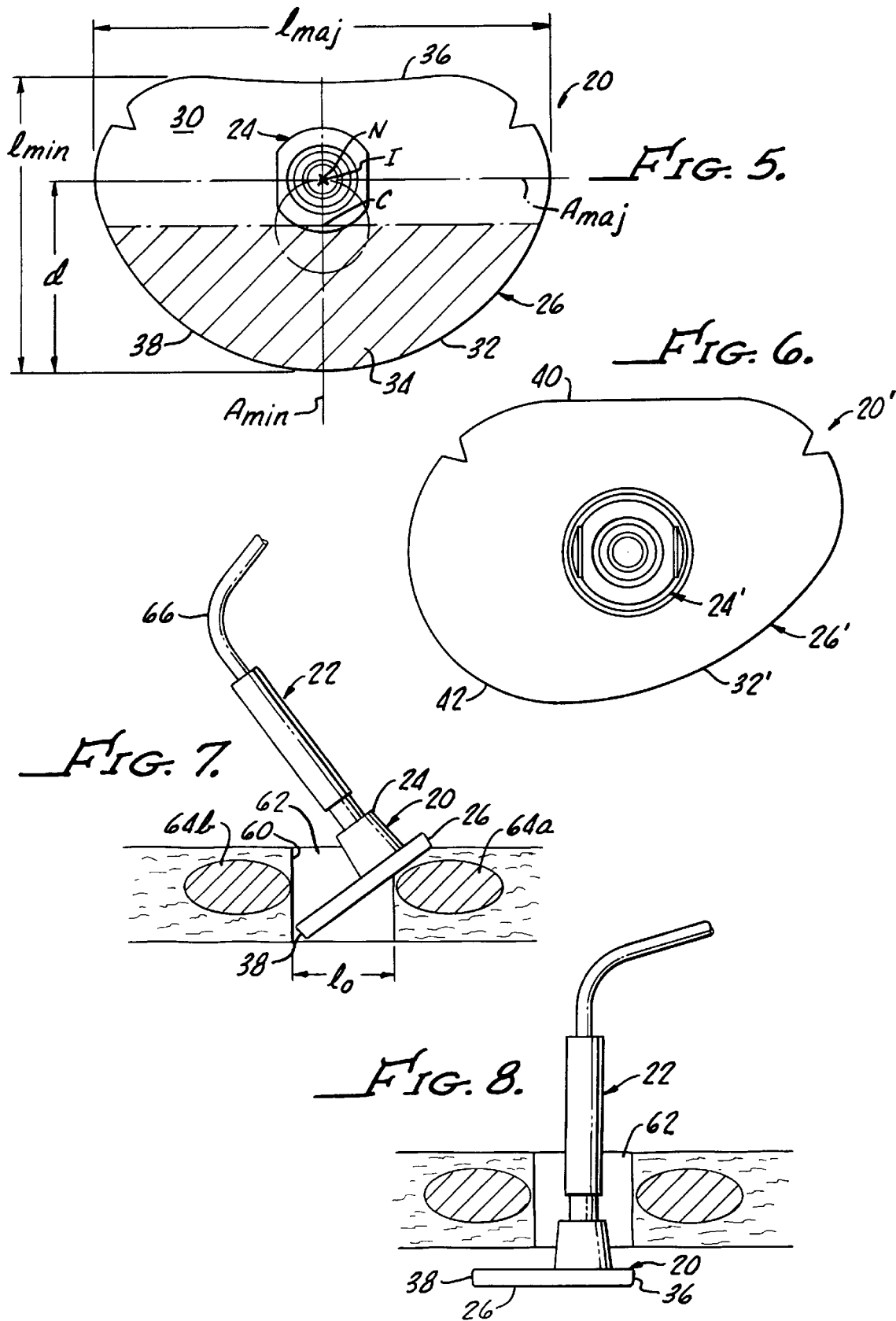

MINIMALLY INVASIVE VALVE ANNULUS SIZER

FIELD OF THE INVENTION

The present invention is directed to apparatus and associated methods for measuring the size of a heart valve annulus during annuloplasty surgery. Heart valve annuluses are measured in order to select a properly sized annuloplasty ring which is then implanted to repair a defective valve of the heart, such as the mitral valve or the tricuspid valve.

BACKGROUND OF THE INVENTION

The heart has four valves—two on the right (the pulmonary and tricuspid) and two on the left (the aortic and mitral)—that control the flow of blood through the chambers of the heart and out to the body. Although any of these valves may fail to function properly, disease most commonly affects the valves on the left side of the heart. The valves may narrow (called stenosis); the valves may not close all the way (causing a backflow of blood called regurgitation); or the valves may close incorrectly (called prolapse). A heart murmur represents the sound that a leaky or narrowed heart valve makes as blood moves through it.

The Aortic and Mitral Valves

Aortic stenosis is a narrowing of the aortic valve, through which blood flows from the left ventricle of the heart to the aorta, the major artery whose branches supply blood to various parts of the body. Sometimes this narrowness is a congenital (i.e., inborn) defect, but more often the valve narrows as a consequence of aging, or of infections, such as rheumatic fever. Aortic stenosis results in the left ventricle having to work harder and harder to push blood out. As this occurs, the muscular walls of the ventricle thicken, increasing their requirement for oxygen. Symptoms of aortic stenosis include chest pain when the oxygen needs exceed the supply from the coronary arteries; fainting (syncope), if the valve becomes very narrow; and congestive heart failure, which usually does not occur unless the valve has been narrowed for many years. Valve replacement, either with a mechanical valve made of metal or plastic or with a valve from a pig, may provide substantial relief from such valvular conditions.

In mitral stenosis, the valve opening between the upper and lower chambers on the left side of the heart has become narrowed. The cause is generally rheumatic fever, which is now rare in most developed countries but is common in many parts of the world, or results from other degenerative diseases and aging. When mitral stenosis occurs, the narrow valve impedes the entry of blood into the left ventricle from the atrium. Pressure builds up behind the valve, leading to an elevation of pressure in the lungs. This in turn may lead to shortness of breath (dyspnea), which is one of the major symptoms of mitral stenosis. Often, however, it occurs without any symptoms.

In aortic regurgitation, the aortic valve fails to close completely after the heart has pumped blood out into the aorta. Blood leaks back from the aorta into the left ventricle. In mitral regurgitation, improper closure causes blood to leak from the left ventricle back into the left atrium. In either case, the valve does not close properly because of a physical change in its shape or its support. This change may be the result of rheumatic fever; an infection (endocarditis), which may leave the valve scarred; or a heart attack, which causes loss of supporting muscle tissue. In the mitral valve, the change may be the result of a heart attack, which causes a loss of muscle tissue, or a spontaneous rupture of one of the muscular chords (chordea tendineae) that normally act as guide wires to keep the mitral valve in place.

Major symptoms of defective mitral valves include fatigue, shortness of breath, and edema. Medications such as digitalis, diuretics, and angiotensin-converting enzyme (ACE) inhibitors can help alleviate symptoms. Some defective mitral valves can be reconstructed or, failing that, replaced by an artificial valve.

The Pulmonary and Tricuspid Valves

In the pulmonary and tricuspid valves, any narrowing is rare and almost always congenital. Leakage, or regurgitation, is unusual, but may occur when use of illicit intravenous drugs leads to infection that damages the valve. The infection, hallmarked by fever, often settles on these two valves because they are the first ones bacteria come in contact with as they travel through the bloodstream. If the valve becomes leaky, swelling of the abdomen and legs may occur. As with other valves, treatment can include replacement, but this is rare and usually not as effective as it is when the aortic or mitral valve is involved.

Treatment

There are several treatments currently used to improve the performance of defective or diseased valves. Drugs such as digitalis medications, vasodilators, diuretics, anticoagulants, and antiarrhythmics may be administered for valve disorders. Rather than being curative, however, the major functions of these drugs are to reduce the severity of the symptoms, possibly reduce the workload of the heart, and prevent complications.

Balloon valvuloplasty may be used to correct narrowing of the mitral valve and occasionally the aortic valve by partially clearing obstructions. In use, a deflated balloon attached to the end of a catheter is introduced through an artery into the heart to the center of the valve opening and then inflated. The inflated balloon presses back the calcium in the valve or corrects the anatomical deformity that has caused the narrowing.

Alternatively, the diseased valve may be replaced with an artificial valve. Valve-replacement surgery is usually recommended when the damage to the valve is sever enough to be potentially life-threatening, as in the case of severe aortic stenosis. The mitral and aortic valves are the heart valves that most often need to be replaced. Artificial valves have been in use since 1952, when Charles Hufnagel successfully replaced a patient's aortic valve with a caged-ball valve.

Another method for treating defective valves is through reconstruction, which is typically used on minimally calcified valves. One type of reconstructive surgery is known as annuloplasty. An annuloplasty is performed to correct mitral valve insufficiency and/or stenosis. Annuloplasty involves implanting an annuloplasty ring on the valve annulus. The annuloplasty ring is designed to support the functional changes that occur during the cardiac cycle: maintaining coaptation and valve integrity in systole while permitting good hemodynamics in diastole.

To perform a successful annuloplasty, the size of the valve annulus where the annuloplasty ring is to be implanted must be accurately measured. Sizing is achieved by measuring the width and the height of the anterior leaflet with sizing obturators or, in the vernacular, valve sizers. Once the size has been determined, a proper annuloplasty ring may be selected and implanted.

A conventional annulus sizer currently used in annuloplasty surgery is illustrated in FIGS. 1 and 2 and is generally referenced with numeral 10. The sizer 10 has a thickness T which is on the order of 0.28 inch and is made of a transparent polymer. The sizer 10 snaps onto a handle 12 with male and female couplers 14 and 16, respectively. The female coupler 16 is formed substantially in the centroid of the somewhat oval-shaped cross-section sizer 10, as shown in FIG. 2. In use, the surgeon estimates the valve annulus size and selects a sizer accordingly. The sizer is snapped onto the end of the handle and guided into proximity of the annulus, which may involve passing the sizer through a relatively small access channel, especially in minimally invasive surgical procedures. The final seating of the sizer in the annulus may necessitate viewing the annulus through the transparent sizer, though the polymer material is not a perfect transmitter of light. The sizer thickness serves to provide tactile feedback to the surgeon for a range of depths of the annulus. That is, the surgeon often pushes the sizer well into the annulus to engage the entire side wall of the sizer, which tends to average the overall resistance to in-and-out movement, and is desired by some surgeons. The central location of the handle connection also balances moments imposed on the sizer as transmitted to the handle. If the sizer is not quite the right size, it is withdrawn and detached from the handle, being replaced by a different sizer. In the insertion or withdrawal steps, the sizer may be accidentally pried off the handle because of the snap fit, though the same attribute of ease of detachment is viewed as a plus to enable rapid switching of different sizers. Additionally, with the trend toward smaller and smaller access channels, the size of devices such as sizers and valves is becoming a limiting factor.

Accordingly, in view of the foregoing, it is an object of the present invention to provide annulus sizers which eliminate many of the drawbacks associated with conventional sizers.

It is an additional object of the present invention to provide annulus sizers which enable a surgeon to clearly view a surgical field.

It is yet another object of the present invention to provide annulus sizers which facilitate annuloplasty procedures through rapid yet secure attachment to handles.

It is still another object of the present invention to provide methodology which enables surgeons to measure the size of valve annuluses in a minimally invasive manner.

SUMMARY OF THE INVENTION

These and other objects are achieved by the surgical apparatus and associated methods of the present invention which enable a surgeon to accurately measure the size of a valve annulus and then to properly select an annuloplasty ring during annuloplasty surgery.

According to one aspect of the invention, an annulus sizer includes a sizing portion with a coupling portion disposed on a proximal surface thereof. The sizing portion measures a valve annulus, and the coupling portion attaches to a handle. The sizing portion has a thickness on the order of about 0.1 inch. The relatively small thickness of the sizer facilitates minimally invasive annuloplasty surgery. For example, rather than accessing the heart through a sternotomy, a relatively small incision may be made intercostally through which the relatively thin sizer of the invention may be inserted. In addition, the relatively thin sizing portion minimizes optical distortion therethrough so that the surgeon is able to view the surgical field more clearly.

In accordance with another aspect of the invention, the coupling portion may be disposed on the sizing portion at a location which is offset from the center of the sizer. Accordingly, an enlarged viewing area is defined on the sizing portion. Augmenting the advantages of low optical distortion, the enlarged viewing area enhances the surgeon's view of the surgical field.

Another aspect of the invention involves securely attaching the sizer to a handle to prevent inadvertent detachment. This is accomplished by providing the coupling portion with threading to engage with threading of the handle. The threading preferably has a large pitch so that the sizer can be attached to the handle in just a couple of turns and in a secure and reliable manner. As time is of the essence during annuloplasty surgery, this secure yet quick attachment feature of the invention is particularly advantageous.

Other aspects, features, and advantages of the present invention will become apparent to those persons having ordinary skill in the art to which the present invention pertains from the following description taken in conjunction with the accompanying drawings.

BRIEF DESCRIPTION OF THE DRAWINGS

FIG. 5 is a plan view of the annulus sizer of the invention, particularly illustrating a preferred handle attachment location which enhances visibility during minimally invasive procedures;

FIG. 6 is a plan view of another exemplary annulus sizer of the present invention, particularly illustrating a sizer for measuring a tricuspid valve annulus;

FIG. 7 is a diagrammatic view of a surgical implement for measuring annuluses during a minimally invasive procedure with a patient shown in cross section, particularly illustrating a step of entering a chest cavity intercostally; and FIG. 8 is a view similar to that of FIG. 7, particularly illustrating a subsequent step in the minimally invasive annulus measuring procedure, particularly illustrating a sizer of the present invention within the chest cavity.

DESCRIPTION OF THE PREFERRED EMBODIMENTS

Figure 1:
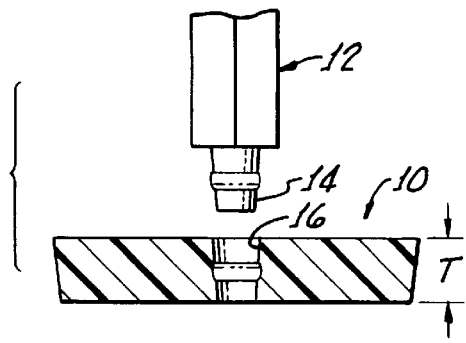
FIG. 1 is a cross-sectional view of a conventional annulus sizer and handle end.
Figure 2:
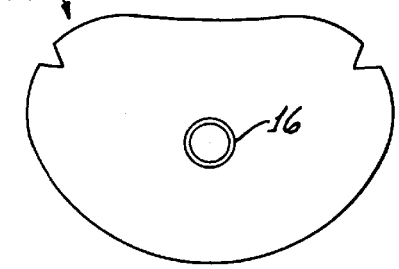
FIG. 2 is a plan view of the conventional annulus sizer.
Figure 3:
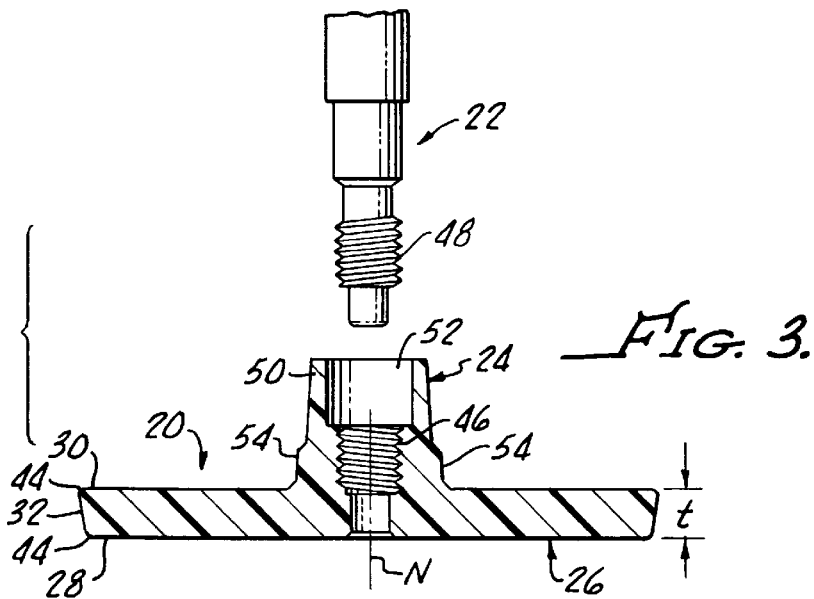
FIG. 3 is a cross-sectional view of an exemplary annulus sizer and handle end for use during minimally invasive surgical procedures in accordance with the present invention, particularly illustrating a sizer for measuring a mitral valve annulus.

Referring to the drawings in more detail, an exemplary embodiment of a valve sizer 20 of the present invention is illustrated in FIG. 3 in conjunction with a surgical handle 22. Exemplary sizer 20 includes a coupling portion 24 and a sizing portion 26. The coupling portion 24 includes structure for releasably attaching to the handle 22, which will be discussed in more detail below. With additional reference to FIG. 4, the sizing portion 26 is utilized to determine the size of a valve annulus during annuloplasty surgery. Exemplary sizer 20 is configured to measure the annulus of a mitral valve, which will be discussed in more detail below.

Exemplary sizing portion 26 is substantially flat and thin, with a distal surface 28, a proximal surface 30, and a thin peripheral side wall 32 extending between the surfaces. As shown, the coupling portion 24 is disposed on the proximal surface 30 of the sizing portion 26, and may be integrally molded together therewith. The sizing portion 26 has a thickness t that is substantially less than the thickness of conventional sizers, as discussed below.

Exemplary sizer 20 is made from biocompatible material that is also preferably optically transparent and substantially rigid. An exemplary material for the sizer 20 is polysulfone, or other similar thermoplastic. The thickness t of the sizing portion 26 is preferably minimized while still retaining substantial strength to prevent substantial flexing or bending or to prevent breakage. Generally speaking, the thickness t of the sizing portion 26 may be less than about 0.2 inch but is preferably on the order of about 0.1 inch. Depending upon the material from which exemplary sizing portion 26 is made, the thickness t may be substantially less than 0.1 inch. In a commercial embodiment of the sizer 20, the thickness t is about 0.115 inch.

Relatively thick conventional sizers distort the field of view due to refraction of light through the thermoplastic. In addition, conventional sizers are too thick to be utilized in many minimally invasive procedures because of the minimal size of openings to access the heart. In contrast, the minimized thickness t of exemplary sizer 20 of the present invention not only minimizes optical distortion but also facilitates insertion through small surgical openings common in minimally invasive procedures, an example of which will be discussed below.

Referencing FIG. 5, the sizing portion 26 of exemplary sizer 20 has a center C which may be defined as lying at the center of a line of symmetry dividing the substantially bean-shaped sizing portion 26. The line of symmetry is vertical in FIG. 5 and coincides with a line denoting a minor axis $A_{min}$. As shown, the coupling portion 24 is preferably positioned on the sizing portion 26 at a location which is offset toward a concave edge of the sizing portion 26 from the center C. Accordingly, an enlarged viewing area is defined on the sizing portion 26. The enlarged viewing area is referenced by numeral 34 and is graphically represented in the drawings by the shaded area of the sizing portion 26. Those of skill in the art will recognize that the location of the coupling portion 24 with respect to the sizing portion 26 may be generalized as offset away from a centroid, leaving a larger viewing area, such as indicated at 34. In other words, though common, the particular bean shape of the present sizing portion 26 is exemplary only, and other sizer shapes are known.

As discussed above, conventional sizers have a socket for attaching to a handle disposed substantially at the center of the sizer. This limits a viewing area around the socket to a relatively narrow and concentric ring. In contrast to conventional sizers, exemplary sizer 20 of the present invention greatly increases the percentage of the field of view which a surgeon may see. Accordingly, the enlarged viewing area 34, coupled with the minimal thickness t of the sizing portion 26 which minimizes optical distortion, enhances the ability of a surgeon to position the sizer in a valve annulus and to determine its size accurately.

Although exemplary sizer 20 may be configured in any desired manner, it is preferable for the sizing portion 26 to have a shape which is analogous to the shape of a healthy valve annulus and/or the shape of an annuloplasty ring. Accordingly, the sizing portion 26 may be noncircular in shape. More specifically, the sizing portion 26 for mitral valve annuluses is typically shaped somewhat like a kidney bean and, as shown in FIG. 5, defines a major axis $A_{maj}$ and the aforementioned minor axis $A_{min}$, which axes have an intersection I. The major axis $A_{maj}$ is defined generally along the greater of the two dimensions of the sizer 20 (i.e., the horizontal dimension from apogee to apogee), and the minor axis $A_{min}$ is defined generally along the lesser of the two dimensions of the sizer 20 (i.e., the vertical dimension). Again, the kidney-shaped mitral-valve sizer 20 shown in FIG. 5 is substantially symmetrical about the minor axis $A_{min}$.

Given the major and minor axes $A_{maj}$ and $A_{min}$ defined on exemplary sizer 20 of the invention, the coupling portion 24 may be positioned on the sizing portion 26 substantially at or near the intersection I. In other words, the coupling portion 24 may have an axis N defined therethrough (see FIG. 3) which passes substantially through the intersection I of the axes $A_{maj}$ and $A_{min}$.

With continued reference to FIG. 5, as mentioned above, the coupling portion 24 may be offset from the center C. In this regard, the coupling portion 24 is preferably offset from the center C along the minor axis $A_{min}$ and positioned substantially on the major axis $A_{maj}$. Depending upon the preferred embodiment of the sizer 20, the location at which the coupling portion 24 is disposed on the sizing portion 26 may be further offset from the center C along the minor axis $A_{min}$ toward the side wall 32. Alternatively, the coupling portion 24 may be offset from the center C in any direction (indiscriminate of the axis $A_{maj}$ and $A_{min}$) to define an enlarged viewing area on the sizing portion 26.

Depending upon the configuration of the sizing portion 26, the side wall 32 may have a plurality of different portions or segments defined therealong and separated by transitions in shape. For example, in the kidney-shaped configuration of the sizing portion 26 illustrated in FIG. 5, the side wall 32 may have a concave side 36 and a convex side 38. Although illustrated as a subtle curvature, the concave side 36 of the side wall 32 curves inwardly toward the center C at or near the minor axis $A_{min}$. Conversely, the convex side 38 of the side wall 32 curves outwardly from the center C at or near the minor axis $A_{min}$. Further to the description provided above, the coupling portion 24 may be positioned on the sizing portion 26 at a location which is closer to the concave side 36 than to the convex side 38 of the side wall 32.

To further define the exemplary configuration of sizer 20 illustrated in FIG. 5, the sizing portion 26 has a length $l_{maj}$ defined along the major axis $A_{maj}$ and a length $l_{min}$ defined along the minor axis $A_{min}$, with the major-axis length $l_{maj}$ being greater than the minor-axis length $l_{min}$. The relationship between the respective magnitudes the major- and minor-axis lengths $l_{maj}$ and $l_{min}$ is preferably defined as a ratio of about 3:2 to about 4:3. More desirably, and stated a different way, the major-axis length $l_{maj}$ is about 1.2 to about 1.5 times greater than the minor-axis length $l_{min}$. Exemplary sizer 20 may be configured in accordance with other ratios of the lengths $l_{maj}$ and $l_{min}$ for use in specific valve-sizing applications. The major-axis length $l_{maj}$ corresponds to and is used to measure the width of the anterior leaflet of a valve, and the minor-axis length $l_{min}$, corresponds to and is used to measure the height of the anterior leaflet.

In addition to lengths $l_{maj}$ and $l_{min}$, a distance d, which is defined as the distance the major axis $A_{maj}$ is from an apogee of the convex side 38 (i.e., the point at or near the intersection of the minor axis $A_{min}$ and the convex side 38), may be used to further define the configuration of the sizing portion 26. The magnitude of the apogee distance d is greater than 50% of the minor-axis length $l_{min}$ and is preferably greater than at least 60% to 70% of the minor-axis length $l_{min}$. In a preferred embodiment of a sizer 20 for measuring mitral-valve annuluses, the apogee distance d is about 65% of the minor-axis length $l_{min}$.

To measure the size of a valve annulus accurately, a plurality of sizers 20 of different dimensions is made available to a surgeon during an annuloplasty surgery, with each of the sizers corresponding to the size of an annuloplasty ring. As known in the art, annulus sizers are numbered according to the major-axis length $l_{maj}$ in millimeters. The numbering system for mitral-annulus sizers, for example, includes 24, 26, 28 . . . 40. In accordance with a commercial embodiment of the present invention, a No. 36 sizer, for example, may have a major-axis length $l_{maj}$ of about 1.5 inches, a minor-axis length $l_{min}$ of about 1.0 inch, and an apogee distance d of about 0.65 inch.

Contrasting the substantially symmetrical configuration of the sizing portion 26 of exemplary sizer 20 for use in measuring a mitral valve annulus illustrated in FIG. 5, the sizing portion may be configured substantially asymmetrically as shown in FIG. 6, which illustrates an exemplary embodiment of a valve annulus sizer of the invention for use in measuring a tricuspid valve annulus. Exemplary tricuspid sizer shown in FIG. 6 is indicated with numeral 20 with the addition of a prime ('). The sizing portion 26' of exemplary tricuspid sizer 20' includes a substantially linear side 40 and an irregular convex side 42. The irregularly shaped convex side 42 provides an enlarged viewing area on the sizing portion 26'. The coupling portion 24' is also shown in FIG. 6.

Further referencing FIG. 3, the side wall 32 may taper from the distal surface 28 to the proximal surface 30. The tapered side wall 32 preferably angles outwardly so that the proximal surface 30 is larger than the distal surface 28. The edges 44 defined between the side wall 32 and each of the surfaces 28 and 30 is preferably rounded to be substantially atraumatic.

With continued reference to FIG. 3, the coupling portion 24 may be configured to be releasably attachable to the handle 22. For example, the coupling portion 24 may include a threaded socket 46 for engaging with threading 48 disposed on a distal end of the handle 22. The threading 46 and 48 preferably has a pitch which allows the sizer 20 to engage securely with the handle 22 in relatively few turns, for example, two or three turns. For example, the threading 46 and 48 may have a pitch of about 20 to 25 turns per inch. To facilitate a secure engagement, the coupling portion 24 preferably extends outwardly away from the proximal surface 30 of the sizing portion 26, thereby defining a tubular boss 50.

Figure 4:
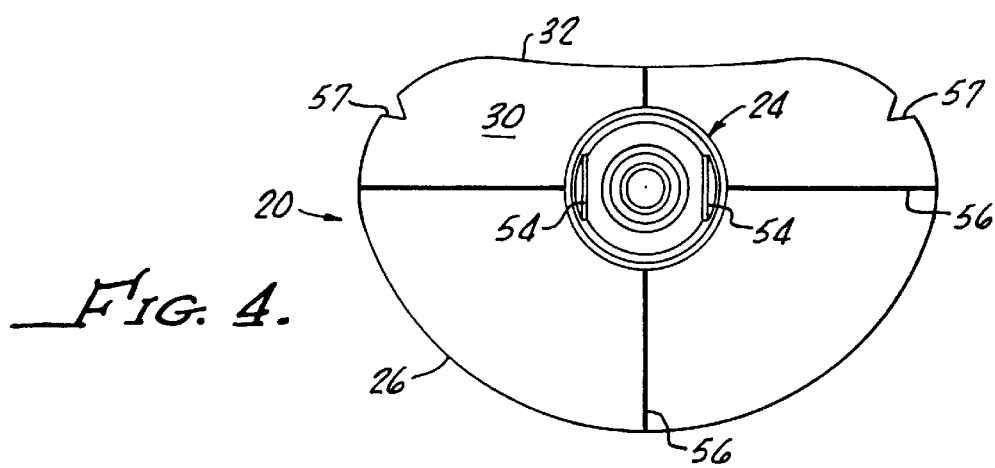
FIG. 4 is a plan view of the annulus sizer of the invention.

As shown in FIGS. 3 and 4, a central channel 52 (with axis N) may extend through the coupling portion 24, as well as through the sizing portion 26. The coupling portion 24 may further include a pair of diametrically opposed planar surfaces 54, which are clearly shown in FIG. 4. Surfaces 54 may be used for grasping the sizer 20 with a tool other than the handle 22, for example, with a forceps. As shown in FIG. 4, the sizing portion 26 desirably includes cross hairs 56 formed on the proximal surface 30 to aid in making vertical and horizontal measurements in a valve annulus. In addition, the sizing portion 26 may include a pair of notches 57 corresponding to the commissures of a valve annulus for purposes of locating and orienting the sizing portion 26 in the valve annulus.

Although it may be used in any type of annuloplasty surgery, exemplary sizer 20 of the present invention is particularly useful in minimally invasive procedures. In annuloplasty surgery, a plurality of annuloplasty rings, each of a different size as known in the art, are provided. A plurality of sizers 20 are also made available to the surgeon. Each of the sizers 20 has a size corresponding to one of the annuloplasty rings.

Referencing FIGS. 7 and 8, the heart of the patient is then accessed, which may be carried out through any type of conventional sternotomy or through a mini-thoracotomy. Access to the chest cavity is preferably accomplished in a minimally invasive manner, for example, through an intercostal incision 60 which defines an opening 62 between adjacent ribs 64a and 64b. If desired, a retractor or a trocar (not shown) may be employed to maintain patency of the opening 62. In addition, cartilage may be removed in forming the opening 62, if desired and as known in the art.

The surgeon may then access the heart and the valve annulus of the defective valve. As mentioned above, the valve annulus needs to be measured to select a properly sized annuloplasty ring. To measure the annulus, one of the sizers is selected and positioned in the annulus. If the surgeon determines that this is not a proper sizer, another differently sized sizer may be selected and positioned in the annulus. This process, which is discussed in detail below, may be repeated until the surgeon determines the size of the annulus.

To carry out this procedure, one of the plurality of sizers 20 is selected and attached to the handle 22 as described above. The handle 22 is preferably made from a malleable material so that a bend 66 may be formed in the handle 22 to facilitate the procedure. To minimize trauma to the patient, the size of the opening 62 is preferably minimized. In this regard, the opening 62 preferably has a length $l_o$ which is less than the minor-axis width $l_{min}$ of the sizing portion 26; for example, length $l_o$ may be less than about an inch or, more preferably, less than about three-quarters of an inch.

In order to insert the sizer 20 through an opening 62 with a length $l_o$ which is less than the minor-axis length $l_{min}$ of the sizing portion 26, the sizer 20 may be tilted obliquely to the opening 62 and then inserted through the opening 62, with the convex side 38 defining a leading edge. When the convex side 38 has passed through the opening 62, the sizer 20 may be tilted in a reverse manner while urging the concave portion 36 (which defines a trailing edge) through the opening 62. When through, the sizer 20 may be positioned on or above the valve annulus to determine its size. The enlarged viewing area 34 enhances the surgeon's ability to view the surgical field with or without visual aids. The sizer 20 may be removed from the patient by essentially reversing the foregoing insertion procedure.

The minimized thickness t of the sizing portion 26 facilitates the insertion and the removal of the sizer 20 through the relatively narrow opening 62. In addition, as the surgeon's field of view is limited by the size of the opening 62, he or she may look through the transparent sizing portion 26 with minimal distortion. The threaded connection between the coupling portion 26 and the handle 22 ensures a secure attachment, which is beneficial in tight minimally invasive working environments. For example, pressure may be applied on the sizer 20 while being removed through the opening 62, which pressure could possibly disengage conventionally attached sizers. In addition, the large pitch of the threading 46 and 48 allows the surgeon to quickly remove and reattach different sizers in a secure and reliable manner.

Those skilled in the art will understand that the embodiments of the present invention described above exemplify the principles of the invention and do not limit the scope of the invention to those embodiments of the surgical apparatus specifically illustrated in the drawings and described above. The exemplary embodiments provide a foundation from which numerous alternatives and modifications may be made, which alternatives and modifications are also within the scope of the present invention as defined in the appended claims.

What is claimed is:

1. A sizer for measuring a valve annulus, said sizer comprising:
   a coupling portion for releasably attaching to a handle; and
   a sizing portion for measuring a valve annulus;
   said coupling portion being disposed on said sizing portion; and
   said sizing portion having a thickness of less than about 0.2 inch.

2. A sizer as claimed in claim 1 wherein said sizing portion is optically transparent.

3. A sizer as claimed in claim 1 wherein said sizing portion has a major axis and a minor axis;
   said sizing portion having a length along said major axis at least about 1.2 times greater than a length along said minor axis.

4. A sizer as claimed in claim 3 wherein said sizing portion has a major axis and a minor axis with an intersection;
   said coupling portion being positioned substantially at said intersection.

5. A sizer as claimed in claim 1 wherein said sizing portion is substantially flat and thin, with a distal surface, a proximal surface, and a thin peripheral side wall.

6. A sizer as claimed in claim 5 wherein said proximal surface having a center, and said coupling portion is positioned on said sizing portion at a location which is offset from said center.

7. A sizer as claimed in claim 6 wherein said sizing portion has a major axis and a minor axis;
   said coupling portion being offset from said center along said minor axis.

8. A sizer as claimed in claim 7 wherein said coupling portion is positioned substantially on said major axis.

9. A sizer as claimed in claim 1 wherein said sizing portion has a distal surface, a proximal surface, and a side wall;
   said surfaces being substantially kidney shaped such that said side wall has a concave side and a convex side.

10. A sizer as claimed in claim 9 wherein said coupling portion is positioned on said sizing portion at a location which is closer to said concave side than to said convex side of said side wall.

11. A sizer as claimed in claim 9 wherein said sizing portion has a major axis and a minor axis;
    said concave side being offset from said minor axis.

12. A sizer as claimed in claim 1 wherein said sizing portion has a distal surface, a proximal surface, and a side wall;
    said side wall tapering from said distal surface to said proximal surface.

13. A sizer as claimed in claim 1 wherein said sizing portion has a distal surface, a proximal surface, and a side wall defining an edge with each of said surfaces;
    said edges being rounded.

14. A sizer as claimed in claim 1 wherein said coupling portion includes threading.

15. A sizer as claimed in claim 1 wherein:
    said sizing portion has a major axis and a minor axis with an intersection; and
    said coupling portion has a central axis;
    said coupling portion being positioned on said sizing portion such that said central axis substantially intersects said intersection.

16. A sizer for measuring a valve annulus, said sizer comprising:
    a sizing portion for measuring a valve annulus and having a distal surface, a proximal surface, and a side wall having a thickness which is less than about 0.2 inch, the side wall defining a shape having a major axis and a minor axis, and a geometric center defined at the intersection of the major and minor axes; and
    a coupling portion for releasably attaching to a handle and disposed on said sizing portion at a location which is generally on the minor axis and spaced from the nearest side wall a distance which is less than or equal to 40% of the minor axis.

17. Surgical apparatus for measuring a valve annulus, said surgical apparatus comprising:
    a handle; and
    a sizer including a coupling portion for attaching to said handle and a sizing portion for measuring a valve annulus;
    said coupling portion being disposed on said sizing portion; and
    said sizing portion having a thickness of less than about 0.2 inch.

18. Surgical apparatus as claimed in claim 17, wherein said coupling portion is releasably attachable to said handle.

19. Surgical apparatus as claimed in claim 18, wherein said coupling portion includes threading.

20. Surgical apparatus as claimed in claim 18, further comprising a plurality of said sizers;
    each of said sizers having a sizing portion of predetermined size.

21. Surgical apparatus as claimed in claim 17, wherein said handle is bendable.

22. A method for measuring a valve annulus of a heart, said method comprising the steps of:
    providing a handle;
    providing a plurality of sizers, each of said sizers including a sizing portion having a thickness which is less than about 0.2 inch and a coupling portion disposed on a proximal side of said sizing portion;
    selecting one of said sizers;
    attaching said handle to said coupling portion of said selected sizer; and
    positioning said attached sizer on a valve annulus having a size.

23. A method as claimed in claim 22, further comprising the steps of:
    removing said selected sizer from the valve annulus;
    detaching said handle;
    selecting another one of said sizers;
    attaching said handle to said coupling portion of said selected sizer; and
    positioning said attached sizer on the valve annulus.

24. A method as claimed in claim 23, further comprising the step of:
    repeating said further steps of claim 23 until the size of the valve annulus is determined.

25. A method as claimed in claim 22, further comprising the steps of:
    providing a plurality of annuloplasty rings each of different size; and
    selecting one of said annuloplasty rings which has a size corresponding to that of the valve annulus.

26. A method as claimed in claim 25, further comprising the step of:

implanting said selected annuloplasty ring on the valve annulus.

27. A method as claimed in claim 22, wherein said positioning step comprises the step of:

positioning said attached sizer on a valve annulus of a mitral valve.

28. A method as claimed in claim 27, wherein said positioning step comprises the step of:

positioning said attached sizer on a valve annulus of a tricuspid valve.

29. A method as claimed in claim 22, further comprising the step of:

providing access to the heart.

30. A method as claimed in claim 29, wherein said step of providing access comprises the step of:

providing access to the heart intercostally.

31. A method as claimed in claim 30, wherein said step of providing access comprises the step of:

forming an opening between two adjacent ribs.

32. A method as claimed in claim 31, further comprising the step of:

inserting said selected sizer through said opening.

33. A method as claimed in claim 22, wherein said step of providing a plurality of sizers comprises the step of:

providing a plurality of sizers each of which includes a sizing portion having a length defined along a major axis greater than a length defined along a minor axis.

34. A method as claimed in claim 33, further comprising the steps of:

forming an opening between two adjacent ribs such that said opening has an intercostal length less than said length defined along said minor axis of said sizing portion.

35. A method as claimed in claim 34, further comprising the steps of:

tilting said selected sizer such that said selected sizer is oblique to said opening; and inserting said selected sizer through said opening.

36. A method as claimed in claim 35, wherein said inserting step comprises the step of:

inserting said selected sizer through said opening such that a leading edge of said sizer defined by said minor axis passes through said opening first.

37. A method as claimed in claim 35, wherein said step of providing a handle comprises the step of:

providing a handle which is bendable.

38. A method as claimed in claim 37, further comprising the step of:

bending said handle to facilitate said step of inserting said selected sizer.

39. A method as claimed in claim 22, wherein:

said step of providing a handle comprises the step of:

providing a handle with threading disposed on a distal end thereof;

said step of providing a plurality of sizers comprises the step of:

providing a plurality of sizers each of which includes a coupling portion with threading; and said attaching step comprises the step of:

threading said selected sizer to said handle.

* * * * *